(12) United States Patent
Riek et al.

(10) Patent No.: US 8,394,063 B2
(45) Date of Patent: Mar. 12, 2013

(54) MEDICAL INSTRUMENT

(76) Inventors: Siegfried Riek, Rottweil (DE); Karl-Heinz Bachmann, Villingendorf (DE); Thomas Gaiselmann, Villingendorf (DE)

( * ) Notice: Subject to any disclaimer, the term of this patent is extended or adjusted under 35 U.S.C. 154(b) by 833 days.

(21) Appl. No.: 11/991,794

(22) PCT Filed: Sep. 12, 2006

(86) PCT No.: PCT/EP2006/008856
§ 371 (c)(1),
(2), (4) Date: Mar. 11, 2008

(87) PCT Pub. No.: WO2007/031264
PCT Pub. Date: Mar. 22, 2007

(65) Prior Publication Data
US 2010/0222744 A1    Sep. 2, 2010

(30) Foreign Application Priority Data

Sep. 16, 2005 (DE) .......................... 10 2005 044 468

(51) Int. Cl.
*A61M 5/178* (2006.01)
(52) U.S. Cl. .................................. 604/164.01
(58) Field of Classification Search ......... 604/165.01–165.02, 165.04, 166.01, 604/164.11–166.13, 523, 539; 600/562–564
See application file for complete search history.

(56) References Cited

U.S. PATENT DOCUMENTS

| | | | | |
|---|---|---|---|---|
| 2,907,327 A * | 10/1959 | White | ........................... | 604/60 |
| 4,963,147 A * | 10/1990 | Agee et al. | .................... | 606/170 |
| 5,360,416 A * | 11/1994 | Ausherman et al. | .......... | 604/272 |
| 6,605,047 B2 * | 8/2003 | Zarins et al. | .................. | 600/562 |
| 6,758,824 B1 * | 7/2004 | Miller et al. | .................. | 600/568 |

FOREIGN PATENT DOCUMENTS

| | | |
|---|---|---|
| DE | 28 02 771 A1 | 3/1979 |
| DE | 31 15 192 C2 | 5/1983 |
| DE | 34 11 810 A1 | 10/1985 |
| DE | 33 10 870 C2 | 11/1989 |
| DE | 93 20 803 U1 | 3/1995 |
| DE | 197 50 090 A1 | 6/1999 |
| DE | 697 00 785 T2 | 6/2000 |
| DE | 100 42 606 A1 | 8/2001 |
| DE | 101 17 286 A1 | 10/2002 |
| EP | 0 629 382 B1 | 8/1993 |
| EP | 0 624 381 A2 | 11/1994 |
| EP | 0 892 650 B1 | 1/1999 |
| EP | 1 049 506 B1 | 11/2000 |
| EP | 1 087 690 B1 | 4/2001 |
| WO | 03/080169 A1 | 10/2003 |
| WO | 2005/044357 A1 | 5/2005 |
| WO | 2005/072810 A1 | 8/2005 |

* cited by examiner

*Primary Examiner* — Nicholas Lucchesi
*Assistant Examiner* — Melissa A Snyder
(74) *Attorney, Agent, or Firm* — Nath, Goldberg & Meyer; Jerald L. Meyer; Scott C. Langford

(57) ABSTRACT

A medical instrument comprises a guide tube (10) that can be inserted into a bodily passage of a patient. An elastically flexible cannula may be displaced within an inner axial guide channel of the guide tube (10), the distal tip (52) of the cannula being able to emerge from a lateral opening at the periphery of the guide tube (10) at an angle to the axis of the guide tube (10). The guide tube (10) at its proximal end is accommodated in a handle piece (22) so as to be rotatable about the longitudinal axis of the guide tube.

19 Claims, 4 Drawing Sheets

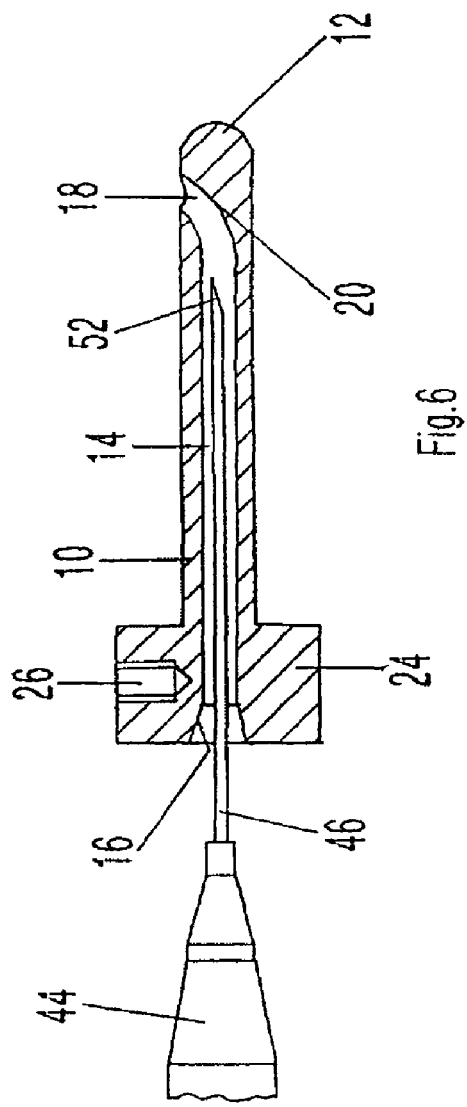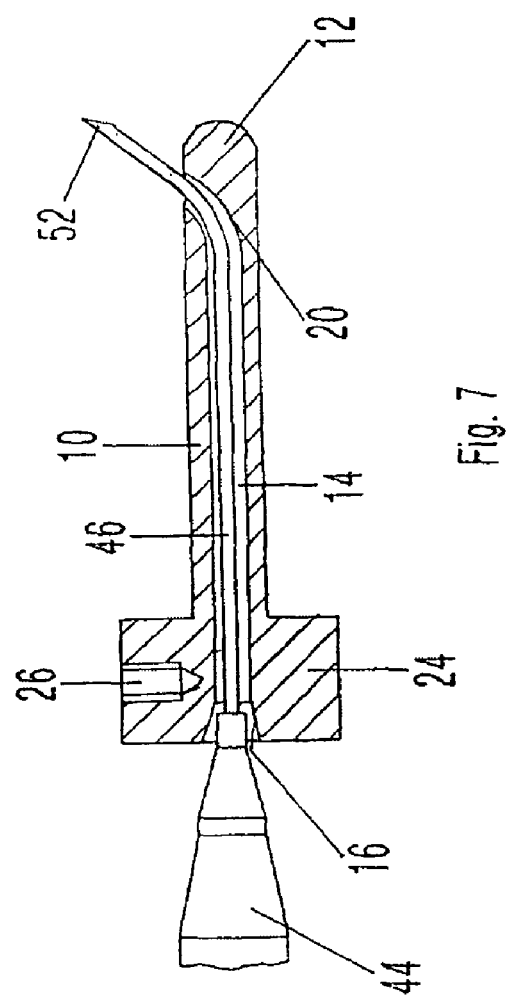

MEDICAL INSTRUMENT

This disclosure relates to a medical instrument which may be inserted into a bodily passage of a patient in order to pierce the wall of the bodily passage or penetrate the wall of the bodily passage with a cannula.

In many medical procedures a cannula is inserted into a bodily passage of the patient in order to pierce the wall of the bodily passage or penetrate the wall of the bodily passage. The cannula may be an injection cannula for administering a medicament, an anesthetic, e.g., into the wall of the bodily passage. One example of such an administration is the injection of a local anesthetic into the wall of the cervical canal for intrauterine procedures such as insertion of an intrauterine coil. Another example is the injection of pharmaceuticals, e.g. the injection of hyaluronic acid into the tissue surrounding the urethra for the treatment of urinary incontinence or the treatment of vesicoureteral reflux in children. The cannula may also be a puncture or biopsy cannula for puncturing the wall of the bodily passage and withdrawing bodily fluids or tissue samples. Such biopsy cannulas may be also be designed as punch cannulas. Puncture biopsies are performed, e.g., for transrectally or transperineally withdrawing tissue from the prostate gland.

In the conventional technique, the cannula is inserted into the bodily passage and must then be inclined at an angle to the axis of the bodily passage in order to pierce the wall of the bodily passage with the distal tip of the cannula. The lumen of the bodily passage generally permits only a relatively small angle between the axis of the bodily passage and the axis of the cannula, so that only a flat penetration into the wall of the bodily passage is possible. In addition, as the result of the small angle between the axis of the bodily passage and the axis of the cannula as well as the irregular shape of the wall surface the puncture site in the wall may be established in the axial direction only in an imprecise manner.

Insertion of an intrauterine coil into the uterus is extremely painful for the patient, e.g. since the insertion device for the intrauterine coil is introduced through the inner opening of the uterus (os internum), which is very sensitive to irritation from dilation. Therefore, it is advantageous to deliver an anesthetic in the region of the inner opening of the uterus. For this purpose an injection cannula may be used to pierce the posterior vaginal fornix near the cervix. This is problematic because the puncture is painful and the injection cannula must be advanced over a relatively great distance through the tissue, in a region in which blood vessels are also present. Another possibility is to introduce an extremely thin injection cannula into the cervical canal and inject the local anesthetic through the wall of the cervical canal and into the musculature of the inner opening of the uterus. The above-described problems in particular may arise that while being advanced in the cervical canal the injection cannula penetrates the wall, since the interior of the cervical canal has a mucous membrane with an irregular surface and the walls practically contact one another. An optimal desired position of the puncture site into the wall of the cervical canal in the region of the inner opening of the uterus is therefore very difficult. Furthermore, the angle of penetration for inserting the cannula through the lumen of the vagina spread by a speculum is limited.

To insert a cannula through the wall of the bodily passage, it is therefore known to provide the cannula in a guide tube. The guide tube has an axial guide channel for the cannula which is angled at the distal end of the guide tube and leads to a lateral opening at the circumference of the guide tube. When the cannula is advanced in the guide channel, the distal tip of the cannula is deflected and emerges laterally through the opening at an angle to the axis of the guide tube. The cannula may thus be inserted into the wall of the bodily passage of the patient at an angle to the axis of the guide tube specified by the opening. When multiple punctures distributed over the circumference of the bodily passage are required, the entire instrument must be rotated about its axis, resulting in difficulty of manipulation.

An instrument is known from WO 96/35464 A1, wherein this problem is remedied by providing multiple axially parallel guide channels in the guide tube which at their distal end are bent outward and open in different angular positions in a distribution over the circumference of the guide tube. Cannulas may be advanced through the various guide channels, and then in the corresponding angular positions penetrate the wall of the bodily passage of the patient without having to rotate the guide tube. However, this instrument is complicated, and the guide tube must have a large diameter on account of the multiple guide channels. In addition, due to the predetermined number of guide channels the instrument is not flexible with regard to the number of punctures and their angular distribution.

The disclosed subject matter provides a medical instrument having a guide tube which may be inserted into a bodily passage for insertion of a flexible cannula, which is easy to manipulate and offers flexible options for use.

This object is achieved according to the invention by use of a medical instrument having a guide tube which may be inserted into a bodily passage of a patient, the guide tube having an inner axial guide channel which leads to a lateral opening at the periphery of the guide tube behind the closed distal end of the guide tube, so that an elastically flexible cannula may be proximally inserted into the guide channel and when advanced in the guide channel emerges laterally at its distal tip through the opening at an angle to the axis of the guide tube.

The medical instrument has a guide tube with an axial guide channel which is bent outwardly at the distal end and ends at a lateral opening at the periphery of the guide tube. A cannula may be pushed through this axial guide channel, and when advanced at the distal end of the guide channel the distal tip of the cannula is deflected from the axis of the guide tube and emerges laterally from the guide tube at an angle to the axis of the guide tube in order to penetrate the wall of a bodily passage of the patient in which the guide tube has been inserted. To enable penetration in a distribution over the circumference at various defined angular positions of the wall of the bodily passage, at its proximal end the guide tube is supported in a handle piece so as to be rotatable about the longitudinal axis of the guide tube. This facilitates manipulation, since the medical practitioner is able to hold the handle piece securely in the hand without having to change the position of the handle piece and thus the position of the hand. The medical practitioner only has to rotate the guide tube in the handle piece to change the angular position of the outlet opening for the cannula at the distal end of the guide tube. The axial position of the distal end of the guide tube, and therefore of the puncture site of the cannula emerging from the guide tube, is determined by the position of the handle piece, so that the axial position of the puncture sites in various angular positions may be easily and reliably maintained.

site of the cannula emerging from the guide tube, is determined by the position of the handle piece, so that the axial position of the puncture sites in various angular positions may be easily and reliably maintained.

The guide tube has only one axial guide channel, and therefore the diameter and cross section of the guide tube do not have to be significantly larger than the diameter and cross section of the inserted cannula. The guide tube may be rotated freely about its longitudinal axis, thus allowing punctures to be made in any given angular position. This results in great flexibility of use, since the number of punctures and their mutual angular position may be freely selected.

At the proximal end of the guide tube that is accommodated in the handle piece a marker is preferably provided which allows the medical practitioner to identify the particular angular position of the guide tube, and thus of the opening for the outlet of the cannula tip.

In one practical design, an essentially radially projecting actuating lever is mounted at the proximal end of the guide tube which allows the guide tube to be easily rotated with sensitivity and at the same time serves as a marker for the rotational angle position.

The guide tube is preferably detachably situated on the handle piece so that the instrument may be disassembled for thorough cleaning and sterilization.

In one practical design, the guide tube has an outer collar at its proximal end which is rotatably supported in a bearing ring at the distal end of the
handle piece. The actuating lever may be inserted into this outer collar, thereby radially passing through a circumferential slit in the bearing ring. The actuating lever is thus used for rotating the guide tube, for indicating the rotational angle position of the guide tube, and for axially securing the guide tube on the handle piece.

In one practical design the handle piece has a holder for a standard syringe, resulting in versatility in use of the instrument. The syringe is preferably axially displaceable in the handle piece between a proximal position and a distal position. In the proximal position the distal tip of the cannula for the syringe is located inside the guide channel of the guide tube, allowing the guide tube to be inserted into the bodily passage of the patient. In the distal position of the syringe the cannula is advanced until its distal tip emerges laterally from the cannula tube and is able to penetrate the wall of the bodily passage of the patient. Manipulation is facilitated when the distal position and the proximal position are each defined by a stop. At the same time, the distal stop defines the length by which the distal end of the cannula projects from the circumference of the guide tube, i.e., the depth of penetration of the cannula into the wall of the bodily passage of the patient.

The disclosed subject matter is explained in greater detail below with reference to one exemplary embodiment illustrated in the drawings, which show the following:

FIG. 6 shows an axial section of the guide tube with the cannula withdrawn; and

FIG. 7 shows an axial section corresponding to FIG. 6, with the cannula advanced forward.

Figure 1:
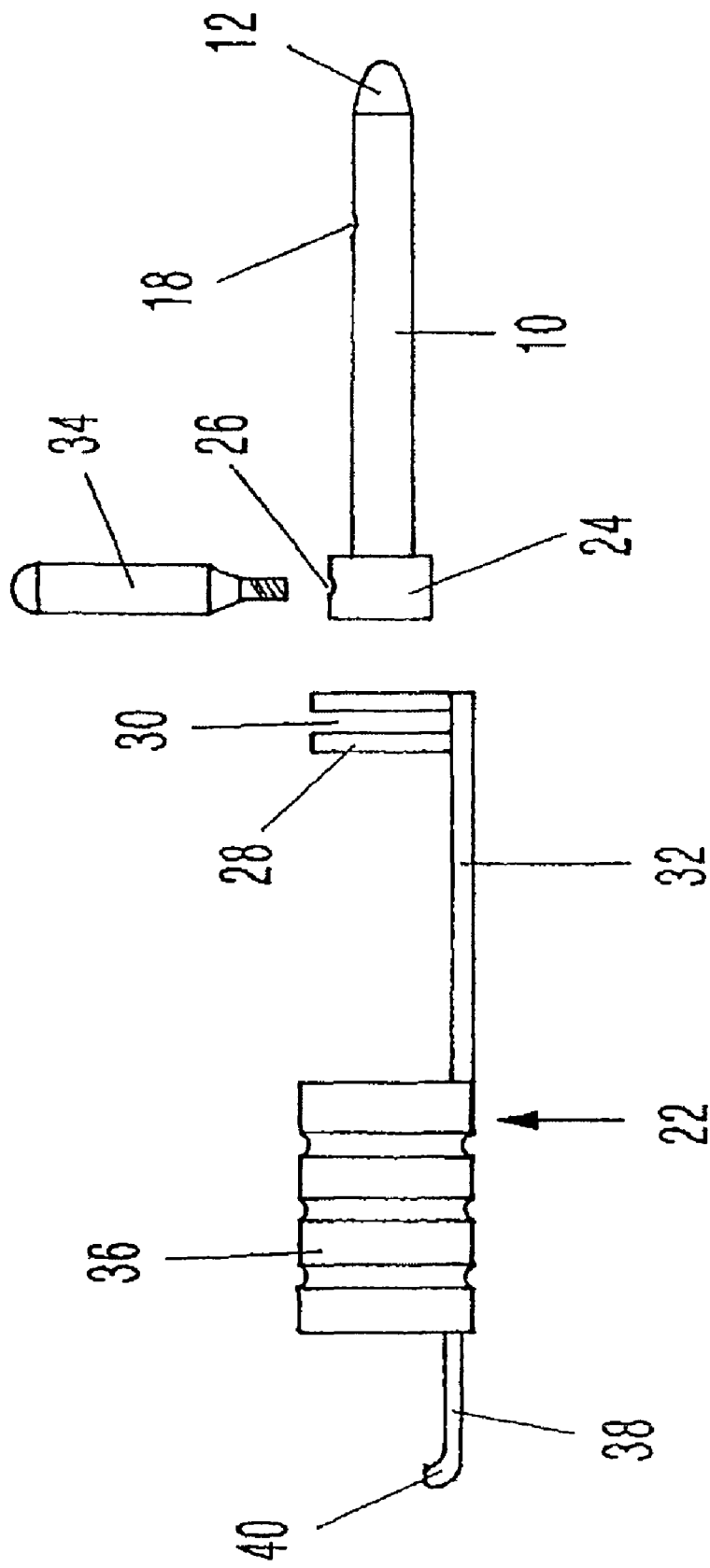
FIG. 1 shows a side view of the instrument in the disassembled state.
Figure 4:
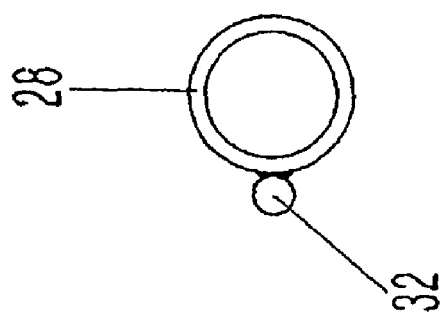
FIG. 4 shows an axial end face view of the right proximal end of the handle piece in FIG. 2.
Figure 2:
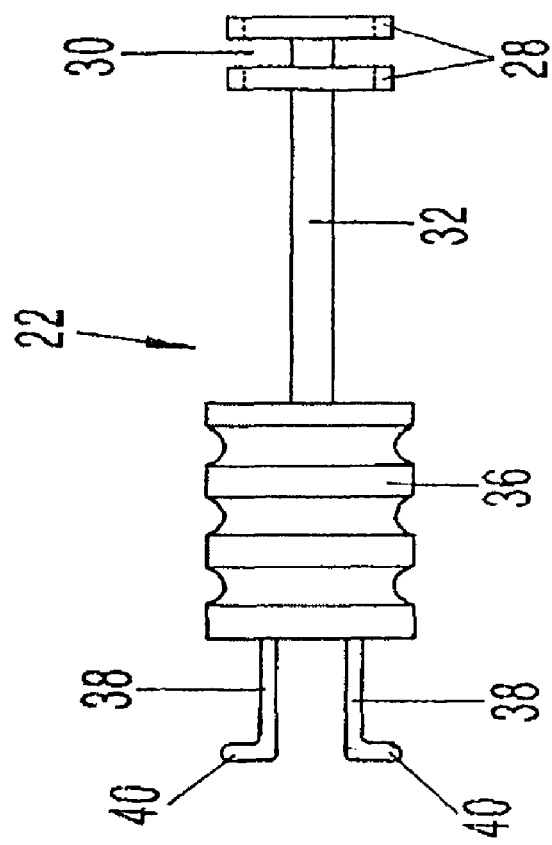
FIG. 2 shows a side view of the handle piece rotated by 90° with respect to FIG. 1.
Figure 3:
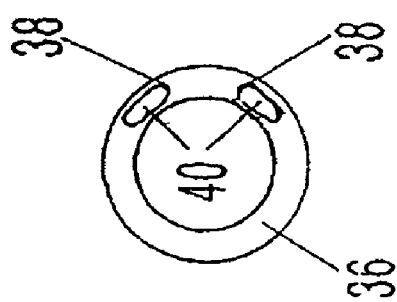
FIG. 3 shows an axial end face view of the left proximal end of the handle piece in FIG. 2.

The medical instrument has a guide tube 10, closed at its distal end 12, and a blunt rounded tip which may also have a slightly conical design. The inner lumen of the guide tube 10 forms a guide channel 14 which at the open proximal end widens to form an insertion cone 16. At the distal end the guide channel 14 leads to a lateral opening 18 provided in the wall of the guide tube 10. The opening 18 is located behind the tapered distal end 12 of the guide tube 10, in the cylindrical lateral surface thereof. A deflecting device 20 is provided inside the guide tube 10, which in the shape of a wedged bevel or an arched, curved ramp forms a continuous transition of the coaxial guide channel 14 to the lateral opening 18. The guide tube 10 is preferably made of stainless steel, but may also be made of a suitable plastic.

The guide tube 10 is rotatably and detachably mounted on a handle piece 22. For this purpose the proximal end of the guide tube 10 has an outer collar 24 which has a circular cross section of enlarged diameter compared to the circular cross section of the guide tube 10. The outer collar 24 is preferably integrally molded onto the guide tube 10 in one piece. A radial blind hole 26 having an internal thread is provided in the cylindrical lateral surface of the outer collar 24. The outer collar 24 is inserted into a bearing ring 28 for the handle piece 22. The inner diameter of the bearing ring 28 corresponds to the outer diameter of the outer collar 24, so that the outer collar 24 is supported in the bearing ring 28 in a rotatably guided manner. The axial length of the outer collar 24 corresponds to the axial length of the bearing ring 28. The bearing ring 28 has a continuous radial circumferential slit 30 running in the circumferential direction which extends over almost 360° of the circumference of the outer collar 24. The circumferential slit 30 may be easily produced by providing the bearing ring 28 as two individual rings which are axially separated by the distance of the width of the circumferential slit 30 and are connected to one another in a narrow angular section by an axial bar 32. The outer collar 24 is axially inserted into the bearing ring 28, in which case the blind hole 26 is located in the axial region of the circumferential slit 30. A radial pin 34 used as an actuating lever is then inserted through the circumferential slit 30 and screwed into the blind hole 26. The pin 34 projects radially beyond the bearing ring 28, allowing the pin 34 to be easily gripped in order to rotate the outer collar 24 and thus the guide tube 10 relative to the bearing ring 28, and thus to rotate the handle piece 22. It is possible to rotate the guide tube 10 by an angle which corresponds to the peripheral angle of the circumferential slit 30, i.e., by an angle of almost 360°. The blind hole 26 and thus the pin 34 are preferably oriented in the same angular position of the guide tube 10 as the opening 18. Thus, the pin 34 also indicates the angular position of the opening 18 with respect to the handle piece 22.

The pin 34 screwed into the blind hole 26 axially holds the outer collar 24 and thus the guide tube 10 in the bearing ring 28, and thus holds same on the handle piece 22. The guide tube 10 may be separated from the handle piece 22 by pulling the pin 34 from the blind hole 26.

The handle piece 22 also has a holder 36 which is designed as a handle and used for guiding the instrument. The holder 36 has the shape of an oblong hollow circular cylinder, and on its outer periphery has circumferential grooves which facilitate gripping the holder 36 as a handle. The axially parallel bar 32, which at its distal end opposite from the holder 36 supports the bearing ring 28 or the two individual rings forming the bearing ring 28, is mounted at the distal end of the holder 36. Two stop clips 38 are mounted at the proximal end of the holder 36. The two stop clips 38 are mounted on the proximal end face edge of the holder 36, offset at an angle relative to one another, and extend axially parallel from the holder 36 in the proximal direction, and at their free proximal ends are bent inward at a right angle, in each case forming a short stop 40.

If the instrument is used for injections, an injection syringe, in particular a standard syringe, e.g. a disposable syringe, is inserted into the instrument. The syringe has a cylinder 42 with a distal cannula attachment point 44 on which a cannula 46 is affixed. A laterally projecting flange 48 is integrally molded onto the proximal end of the cylinder 42. A piston 50 may be displaced in the cylinder 42.

The syringe together with the affixed cannula 46 is inserted from the proximal end into the instrument through the holder 36. The cannula 46 passes into the guide channel 14 of the guide tube 10, facilitated by the insertion cone 16. The cylinder 42 of the syringe is coaxially accommodated in the holder 36. The syringe is inserted into the instrument until the flange 48 at the proximal end of the cylinder 42 is located between the proximal end of the holder 36 and the stops 40 of the stop clips 38. The stops 40 overlap the flange 48 on both sides of the piston 50.

Figure 5:
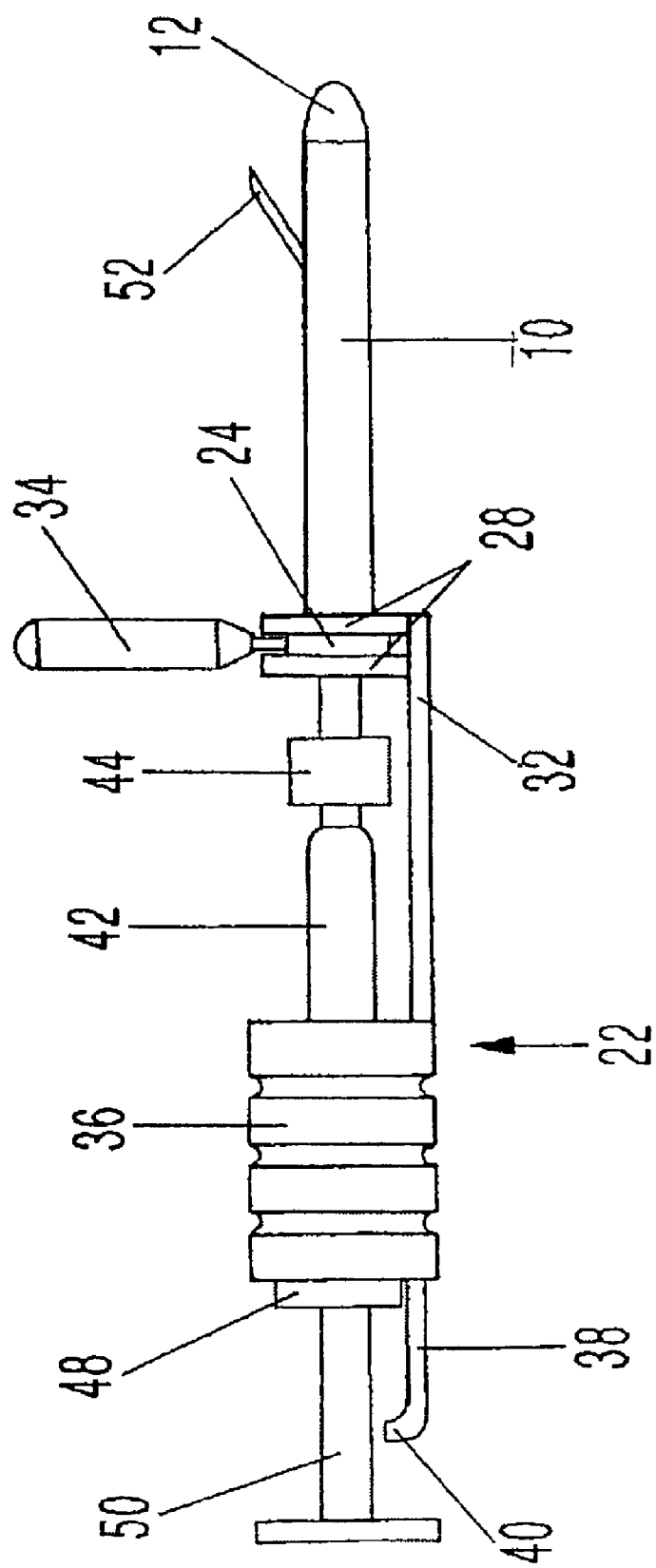
FIG. 5 shows a side view of the instrument with a syringe inserted.

The axial longitudinal dimensions of the instrument are matched to the axial longitudinal dimensions of the syringe, i.e., in particular the cylinder 42 and the cannula 46, in such a way that the distal tip 52 of the cannula 46 is located inside the guide channel 14 behind the deflecting device 20, as shown in FIG. 6, when the cylinder 42 at its flange 48 contacts the stops 40 of the stop clips 38. Since the sharp distal tip 52 of the cannula 46 is situated inside the guide tube 10, the guide tube may be inserted into the bodily passage of the patient without the possibility of injury from the cannula 46. When the guide tube 10 is positioned axially at the injection site, the cylinder 42 of the syringe is advanced forward distally in the holder 36 until the flange 48 stops against the proximal end of the holder 36, as illustrated in FIG. 5. The cannula 46 is likewise advanced forward distally in the guide channel 14, the sharp tip 52 of the cannula 46 being deflected by the deflecting device 20 and emerging laterally from the guide tube 10 through the opening 18, as illustrated in FIG. 7. The stop for the flange 48 on the holder 36 is also defined by the extent to which the tip 52 of the cannula 46 projects from the guide tube 10, thereby specifying the penetration depth of the cannula 46 for the injection. For this injection the medical practitioner holds the instrument at the holder 36 designed as a handle.

The guide tube 10 may be rotated coaxially relative to the handle piece 22 by means of the pin 34, so that the medical practitioner, while holding the handle piece 22 in a fixed position, i.e., with a defined axial position of the opening 18, is able to set the angular position of the opening 18 by rotating the pin 34, and thus is able to set the angular position in which the tip 52 of the cannula 46 emerges from the guide tube 10 and penetrates the wall of the bodily passage. The deflecting device 20 determines the angle of penetration of the tip 52 with respect to the axis of the guide tube 10. Following an injection in a first rotational angle position, the syringe may be withdrawn until it reaches the stops 40, thereby pulling the tip 52 of the cannula 46 back into the guide channel 14. The guide tube 10 may then be rotated into a new angular position, so that by again distally moving the syringe the tip 52 may be reinserted in another angular position and another injection may be performed.

It is obvious that the holder 36 itself does not have to be designed as a handle. It is also possible to mount an additional radially projecting handle on the holder 36 in the manner of a pistol handle, e.g. The design of the holder 36 as a handle has the advantage that the instrument has small radial dimensions, which in many cases facilitates manipulation.

It is also possible to use locking catches which allow an elastic engagement of the guide tube 10 with the handle piece 22 in specified defined rotational angle positions. This simplifies the rotational angle positioning when the cannula 46 is inserted into the wall of the bodily passage. As a rule, however, the friction between the outer collar 24 and the bearing ring 28 is sufficient to hold the guide tube 10 in the particular selected rotational angle position, thus providing the advantage of a continuous angular adjustment.

LIST OF REFERENCE NUMERALS

10 Guide tube
12 Distal end
14 Guide channel
16 Insertion cone
18 Opening
20 Deflecting device
22 Handle piece
24 Outer collar
26 Blind hole
28 Bearing ring
30 Circumferential slit
32 Bar
34 Pin
36 Holder
38 Stop clip
40 Stop
42 Cylinder
44 Cannula attachment point
46 Cannula
48 Flange
50 Piston
52 Syringe

The invention claimed is:

1. Medical instrument comprising:
a guide tube insertable into a bodily passage of a patient, the guide tube having a closed inner axial guide channel internal to the guide tube which terminates in a lateral opening at the periphery of the guide tube behind the closed distal end of the guide tube and terminating with a deflecting channel comprising a guide channel in the shape of a wedged bevel or an arched curved ramp extending from a straight portion to said lateral opening and forming a continuous transition of the inner axial guide channel, the deflecting channel configured to cause an elastically flexible cannula proximally inserted into the guide channel to deflect when advanced in the guide channel and thereby emerge laterally at its distal tip through the opening at an angle to a longitudinal axis of the guide tube established by the deflecting channel; and
a handle piece accommodating the guide tube at the proximal end of the guide tube, with the guide tube rotatable relative to the handle about the longitudinal axis of the guide tube in a rotatably guided manner, wherein the handle piece has a holder for a syringe in which the syringe is axially movable between a proximal position, in which the distal tip of its cannula is withdrawn in the guide channel, and a distal position in which the distal tip of the cannula emerges from the guide tube through the opening.

2. Instrument according to claim 1, characterized in that the guide tube is detachably accommodated in the handle piece.

3. Instrument according to claim 1, characterized in that a marker allows the particular rotational angle position of the guide tube relative to the handle piece to be identified.

4. Instrument according to claim 1, characterized in that the guide tube at its proximal end has an essentially radially projecting actuating lever.

5. Instrument according to claim 4, characterized in that the guide tube at its proximal end has an outer collar rotatably supported in a bearing ring at the distal end of the handle piece.

6. Instrument according to claim 5, characterized in that the bearing ring has a circumferential slit through which the actuating lever passes through radially.

7. Instrument according to claim 6, characterized in that the actuating lever is detachably inserted in the outer collar.

8. Instrument according to claim 1, characterized in that the holder has a stop which limits the axial motion of the syringe in the distal direction.

9. Instrument according to claim 1, characterized in that the holder has a stop which limits the axial motion of the syringe in the proximal direction.

10. Instrument according to claim 1, characterized in that the handle piece has a hollow cylindrical holder which coaxially encloses the cylinder of the inserted syringe.

11. Instrument according to claim 10, characterized in that the holder is designed as a handle.

12. Instrument according to claim 10, characterized in that a handle is mounted on the holder.

13. Instrument according to claim 1, characterized in that: the handle piece has a holder for a syringe, the holder permitting axial movement of the syringe between a proximal position with the distal tip of its cannula withdrawn in the guide channel, and a distal position with the distal tip of the cannula emerging from the guide tube through the opening; and the guide tube at its proximal end has an outer collar, the outer collar rotatably supported in a bearing ring is attached to the holder at the distal end of the handle piece.

14. Instrument according to claim 8, characterized in that the proximal end of the holder forms the distal stop for a flange of the syringe.

15. Instrument according to claim 9, characterized in that a proximally projecting stop for the flange of the syringe is mounted on the holder as a proximal stop.

16. Instrument according to claim 1, further comprising: an elastically flexible cannula capable of deflecting when inserted into the guide channel to deflect when advanced in the guide channel and thereby emerge laterally at its distal tip through the opening at an angle to a longitudinal axis of the guide tube established by the deflecting channel.

17. Medical instrument comprising: a guide tube insertable into a bodily passage of a patient, the guide tube having an inner axial guide channel internal to the guide tube which leads to a lateral opening at the periphery of the guide tube behind the closed distal end of the guide tube and terminating with a deflecting channel;

an elastically flexible cannula, the elastically flexible cannula and the deflecting channel configured to cause the elastically flexible cannula proximally inserted into the guide channel to deflect when advanced in the guide channel and thereby emerge laterally at its distal 1 tip through the opening at an angle to a longitudinal axis of the guide tube established by the deflecting channel; and a handle piece accommodating the guide tube at the proximal end of the guide tube, with the guide tube rotatable relative to the handle about the longitudinal axis of the guide tube in a rotatably guided manner, wherein the handle piece has a holder for a syringe in which the syringe is axially movable between a proximal position, in which the distal tip of its cannula is withdrawn in the guide channel, and a distal position in which the distal tip of the cannula emerges from the guide tube through the opening.

18. Medical instrument comprising: a guide tube insertable into a bodily passage of a patient, the guide tube having a closed inner axial guide channel which terminates in a lateral opening at the periphery of the guide tube behind the closed distal end of the guide tube and terminating with a deflecting channel comprising a curved portion of the axial guide channel within the distal end of the guide tube extending from a straight portion to said lateral opening and forming a continuous transition of the inner axial guide channel, the deflecting channel configured to cause an elastically flexible cannula proximally inserted into the guide channel to deflect when advanced in the guide channel and thereby emerge laterally at its distal tip through the opening at an angle to a longitudinal axis of the guide tube established by the deflecting channel; and a handle piece accommodating the guide tube at the proximal end of the guide tube, with the guide tube rotatable relative to the handle about the longitudinal axis of the guide tube in a rotatably guided manner, wherein the handle piece has a holder for a syringe in which the syringe is axially movable between a proximal position, in which the distal tip of its cannula is withdrawn in the guide channel, and a distal position in which the distal tip of the cannula emerges from the guide tube through the opening.

19. Instrument according to claim 18, characterized in that: the guide tube at its proximal end has an outer collar, the outer collar rotatably supported in a bearing ring is attached to the holder at the distal end of the handle piece.

\* \* \* \* \*